(12) United States Patent
Schnall

(10) Patent No.: US 8,696,619 B2
(45) Date of Patent: Apr. 15, 2014

(54) DRUG DELIVERY DEVICES

(76) Inventor: Robert P. Schnall, Kiryat-Bialik (IL)

(*) Notice: Subject to any disclaimer, the term of this patent is extended or adjusted under 35 U.S.C. 154(b) by 1263 days.

(21) Appl. No.: 11/658,650

(22) PCT Filed: Aug. 10, 2005

(86) PCT No.: PCT/IL2005/000863
§ 371 (c)(1), (2), (4) Date: Jan. 26, 2007

(87) PCT Pub. No.: WO2006/016364
PCT Pub. Date: Feb. 16, 2006

(65) Prior Publication Data
US 2009/0118662 A1    May 7, 2009

Related U.S. Application Data

(60) Provisional application No. 60/667,196, filed on Apr. 1, 2005, provisional application No. 60/599,901, filed on Aug. 10, 2004.

(51) Int. Cl.
*A61M 37/00* (2006.01)
*A61B 17/20* (2006.01)
*A61M 5/00* (2006.01)
*A61M 5/32* (2006.01)

(52) U.S. Cl.
USPC ............. 604/87; 604/46; 604/115; 604/173; 604/272

(58) Field of Classification Search
USPC ......... 604/20–22, 46, 87, 115, 173, 180, 181, 604/185, 272, 306, 307, 96.01, 103.02, 604/103.08; 424/422, 425, 435; 433/80, 433/215, 229
See application file for complete search history.

(56) References Cited

U.S. PATENT DOCUMENTS

| | | | |
|---|---|---|---|
| 2,434,875 A * | 1/1948 | Turnbull et al. | 604/207 |
| 3,136,314 A | 6/1964 | Kravitz | |
| 3,698,561 A * | 10/1972 | Babson | 210/445 |
| 5,405,366 A * | 4/1995 | Fox et al. | 607/50 |
| 5,533,972 A * | 7/1996 | Gyory et al. | 604/20 |
| 6,030,213 A * | 2/2000 | Trop | 433/80 |
| 6,276,935 B1 * | 8/2001 | Funt | 433/80 |

(Continued)

OTHER PUBLICATIONS

"Elastic". Merriam-Webster Online Dictionary. <http://www.merriam-webster.com/dictionary/elastic>.*

*Primary Examiner* — Emily Schmidt
*Assistant Examiner* — Lauren M Peng
(74) *Attorney, Agent, or Firm* — The IP Law-firm of Guy Levi, LLC; Guy Levi

(57) ABSTRACT

A drug delivery device for delivering a drug to a preselected treatment site, includes a rupturable film capsule enclosing a quantity of the drug to be delivered; an array of micro-needles formed with passageways therethrough carried by the device; a covering layer overlying the capsule and forming a fluid-tight seal with the perimeter of the micro-needle array such that when the device is located with the micro-needles facing the treatment site, the application of pressure to the device causes the micro-needles to penetrate the treatment site and the capsule film to rupture to deliver the drug via the passageways to the treatment site; and an open mesh layer adjacent to the array of micro-needles effective, upon rupture of the capsule film, to uniformly distribute the drug to the micro-needles and also to reduce the possibility of clogging of the passageways.

30 Claims, 7 Drawing Sheets

(56) References Cited

U.S. PATENT DOCUMENTS

| | | |
|---|---|---|
| 6,611,707 B1 | 8/2003 | Prausnitz et al. |
| 6,656,147 B1 * | 12/2003 | Gertsek et al. .................. 604/28 |
| 6,881,203 B2 | 4/2005 | Delmore et al. |
| 7,063,693 B2 * | 6/2006 | Guenst .............................. 606/1 |
| 7,186,235 B2 * | 3/2007 | Martin et al. .................... 604/22 |
| 7,315,758 B2 * | 1/2008 | Kwiatkowski et al. ......... 604/21 |
| 2003/0040712 A1 * | 2/2003 | Ray et al. ....................... 604/173 |
| 2003/0083645 A1 * | 5/2003 | Angel et al. ................. 604/890.1 |
| 2003/0135161 A1 * | 7/2003 | Fleming et al. ................ 604/173 |
| 2004/0199103 A1 * | 10/2004 | Kwon ............................. 604/46 |
| 2004/0260251 A1 * | 12/2004 | Chang et al. .................. 604/272 |
| 2005/0165355 A1 * | 7/2005 | Fitzgerald ................ 604/164.08 |
| 2005/0273049 A1 * | 12/2005 | Krulevitch et al. ...... 604/101.02 |

* cited by examiner

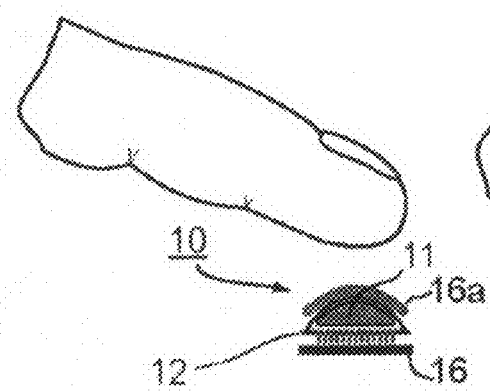 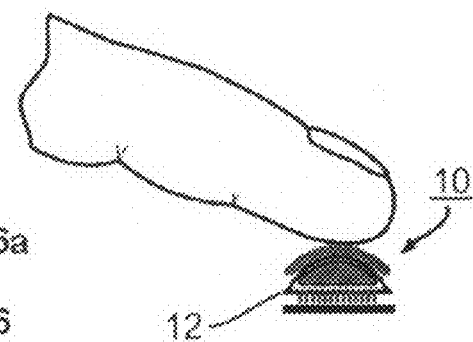
Fig. 5a　　　　　Fig. 5b
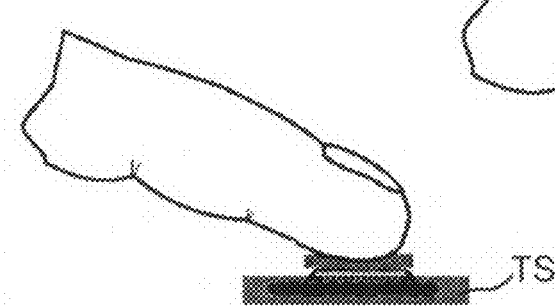 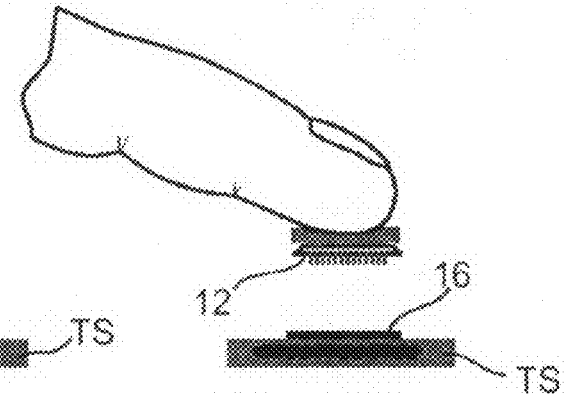
Fig. 5c　　　　　Fig. 5d
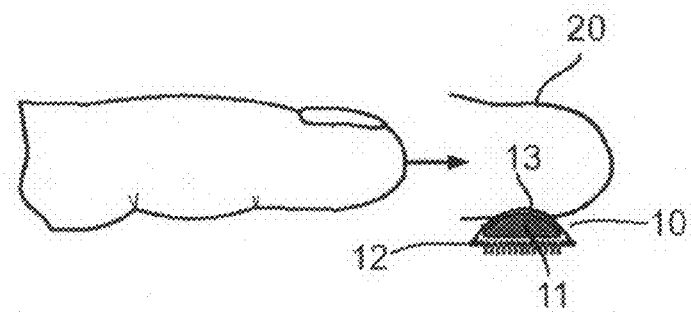
Fig. 6a
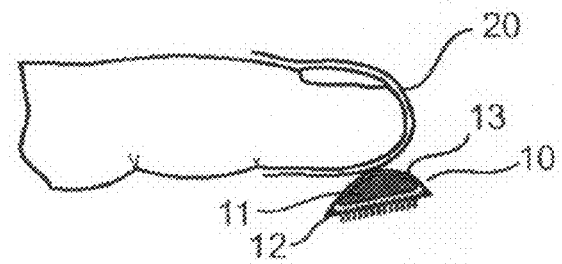
Fig. 6b

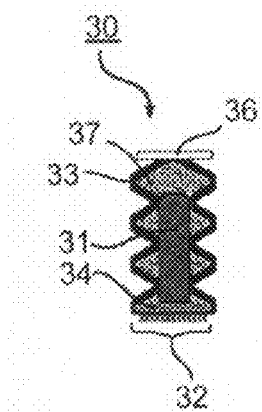
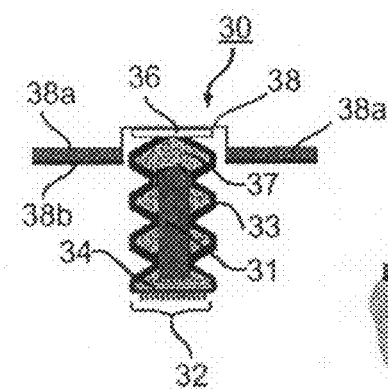
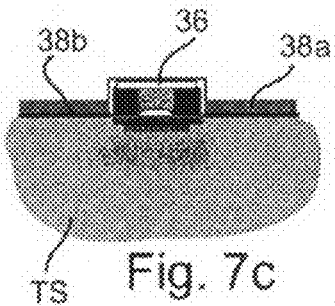
Fig. 7a　　Fig. 7b　　Fig. 7c
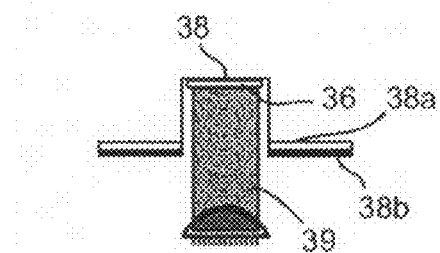
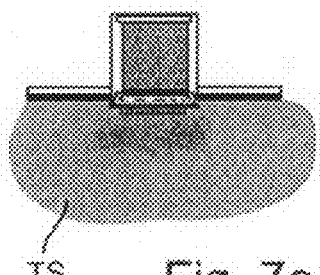
Fig. 7d　　Fig. 7e
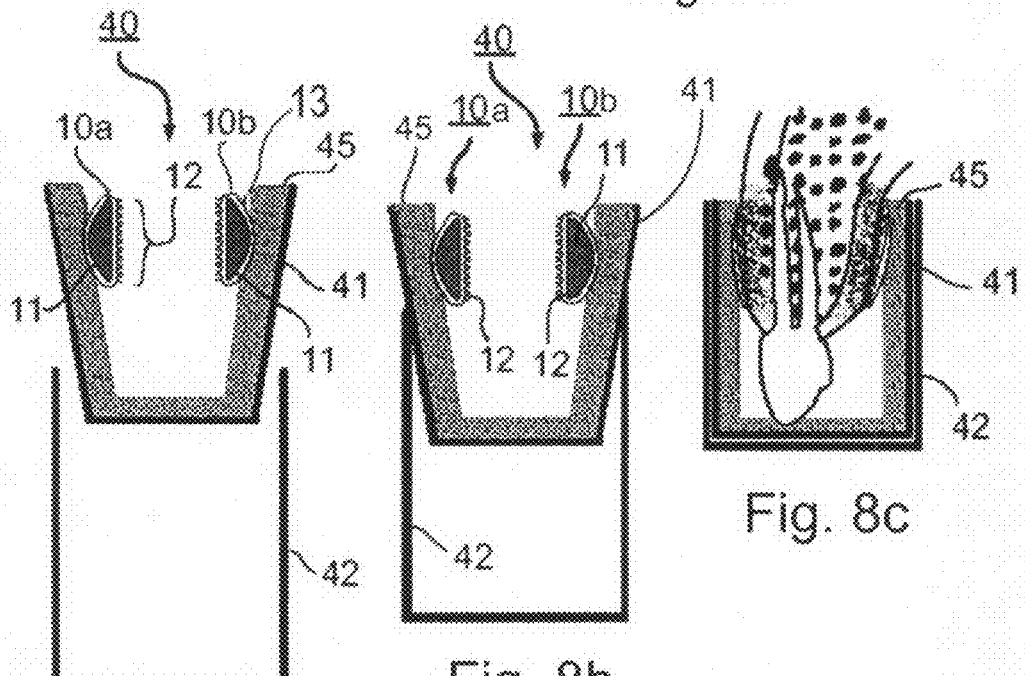
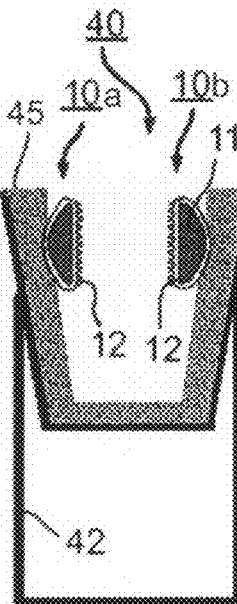
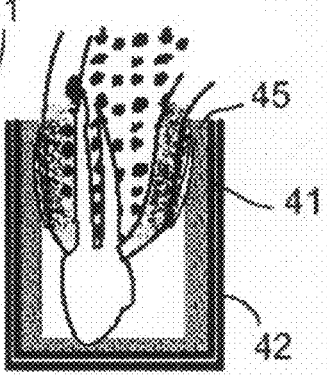
Fig. 8a　　Fig. 8b　　Fig. 8c

DRUG DELIVERY DEVICES

RELATED APPLICATIONS

This Application is a National Phase of PCT Patent Application No. PCT/IL2005/000863 having International Filing Date of Aug. 10, 2005, which claims the benefit of U.S. Provisional Patent Application Nos. 60/667,196 filed on Apr. 1, 2005 and 60/599,901 filed on Aug. 10, 2004. The contents of the above Applications are all incorporated herein by reference.

FIELD AND BACKGROUND OF THE PRESENT INVENTION

The present invention relates to drug delivery devices, and particularly to such devices which deliver the drug via micro-needles and/or iontophoretically.

The conventional way of transdermal drug delivery, namely by hypodermic syringe injection, is very unpleasant and painful, and therefore many alternative ways of drug delivery have been developed. The transdermal patch delivers the drug by diffusion, utilizing merely a concentration gradient as a driving force, but this technique is not very effective with respect to large-molecule drugs, such as proteins and peptides, or drugs which otherwise do not have the proper physiochemical properties for diffusion through the skin.

In recent years, micro-needle type drug delivery devices have been developed for increasing the permeability of the skin by micro-needles having a length of up to about 150 microns, sufficiently short so as not to engage the nerve endings but long enough to penetrate the cornified outer body surface layer. They can be produced from a variety of materials, such as silicon, metal and plastic polymers, in many different sizes and shapes. Examples of such micro-needle type drug delivery devices are described in U.S. Pat. Nos. 3,964,482, 6,611,707, 6,656,147 and 6,558,361, the contents of which are incorporated herein by reference.

An object of the present invention is to provide a drug delivery device of the micro-needle type having a number of advantages, as will be described more particularly below.

BRIEF SUMMARY OF THE PRESENT INVENTION

According to one aspect of the present invention, there is provided a drug delivery device for delivering a drug to a preselected treatment site, comprising: a capsule having a rupturable film enclosing a quantity of the drug to be delivered; an array of micro-needles mounted on a supporting matrix carried by the device, the micro-needles being formed with inlet ends facing the capsule, outlet ends to face the treatment site when the device is located with the micro-needles facing the treatment site, and passageways connecting the inlet and outlet ends, whereby the application of pressure to the device causes the outlet ends of the micro-needles to penetrate the treatment site, the capsule film to rupture, and the inlet ends of the micro-needle to deliver the drug via the passageways to the treatment site; and a porous mesh layer between the capsule and the complete surface of the inlet ends of the micro-needles effective to space the inlet ends of the micro-needles from the capsule, to uniformly distribute the drug to the inlet ends of the micro-needles by a wick action, and, upon the rupture of the capsule film, to reduce the possibility of clogging of the passageways as the drug is delivered therethrough from the capsule to the treatment site.

A number of preferred embodiments of the invention are described below for purposes of example. In most of the described preferred embodiments, the device further comprises an outer deformable fluid-tight layer overlying the capsule and having an outer peripheral edge hermetically secured to the outer peripheral edge of the array of micro-needles so as to enclose the capsule between the array of micro-needles and deformable fluid-tight layer, the deformable fluid-tight outer layer being deformable by pressure to permit rupturing the capsule by the application of pressure thereto.

According to another aspect of the present invention, there is provided a drug delivery device for delivering a drug to a preselected treatment site, comprising:
a rupturable film capsule enclosing a quantity of the drug to be delivered;
an array of micro-needles formed with passageways therethrough mounted on a supporting matrix carried by the device such that when the device is located with the micro-needles facing the treatment site, the application of pressure to the device causes the microneedles to penetrate the treatment site and the capsule film to rupture to deliver the drug via the passageways to the treatment site; and a housing open at one end and configured to be applied to opposing sides of a body part, including the treatment site, with the array of micro-needles facing tissue at the treatment site to which the drug is to be delivered, and further comprising an outer sleeve telescopically receiving the housing and configured with respect to the housing such that axially displacing the outer sleeve towards the housing open end causes opposing sides of the splayed housing to converge and the array of micro-needles to penetrate tissue at the treatment site, and the capsule to rupture to deliver the drug to the underlying tissue.

According to yet another aspect of the present invention, there is provided a drug delivery device for delivering a drug to a treatment site comprising a housing carrying the rupturable film capsule enclosing a quantity of the drug to be delivered, an array of micro-needles formed with passageways therethrough mounted on a supporting matrix carried by the device such that when the device is located with the micro-needles facing the treatment site, the application of pressure to the device causes the micro-needles to penetrate the treatment site and the capsule film to rupture to deliver the drug via the passageways to the treatment site, and an outer deformable fluid-tight layer hermetically secured to the outer peripheral edge of the array of micro-needles so as to enclose the capsule between the array of micro-needles and deformable fluid-tight layer, the deformable fluid-tight outer layer being deformable by pressure to permit rupturing the capsule by the application of pressure thereto; the housing being open at one end and being of a generally splayed configuration and configured to be applied to opposing sides of a tooth, with an array of micro-needles facing tissue at the treatment site or sites to which the drug is to be delivered, and further comprising an outer sleeve telescopically receiving the housing and configured with respect to the housing such that axially displacing the outer sleeve towards the housing open end causes opposing sides of the splayed housing to converge and the array of micro-needles to penetrate tissue at the treatment site, and the capsule to rupture to deliver the drug to the underlying tissue.

According to a further aspect of the present invention, there is provided a drug delivery device configured for delivering a drug to a preselected treatment site within a body lumen, comprising; a rupturable film capsule enclosing a quantity of the drug to be delivered; an array of micro-needles formed with passageways therethrough carried by the device such that when the device is located with the micro-needles facing the treatment site, the application of pressure to the device causes the micro-needles to penetrate the treatment site and the capsule film to rupture to deliver the drug via the passageways to the treatment site; and a balloon which is inflatable at the treatment site to produce the pressure to cause the array of micro-needles to penetrate the treatment site and the capsule to rupture.

According to yet another aspect of the present invention, there is provided a drug delivery device for delivering a drug to a preselected treatment site, comprising a rupturable film capsule enclosing a quantity of the drug to be delivered; an array of micro-needles formed with passageways therethrough mounted on a supporting matrix carried by the device such that when the device is located with the micro-needles facing the treatment site, the application of pressure to the device causes the micro-needles to penetrate the treatment site and the capsule film to rupture to deliver the drug via the passageways to the treatment site; a peelable protective layer covering the micro-needles; and a layer of a hydrogel over and between the micro-needles and covered by the peelable protective layer.

According to yet another aspect of the invention, there is a provided a drug delivery device for delivering a drug to a preselected treatment site, comprising at least one body of a hydrogel wherein the drug to be delivered is held in solution form within the hydrogel such that the drug may be iontophoretically driven into the treatment site.

Further features and advantages of the invention will be apparent from the description below.

BRIEF DESCRIPTION OF THE DRAWINGS

The invention is herein described, by way of example only, with references to the accompanying drawings, wherein:

FIG. 5a-5d illustrates various stages in the use of the device of FIG. 1 for delivering the drug to a treatment site;

FIGS. 6a and 6b illustrate two stages in the use of a device according to the construction on FIG. 1 but modified to facilitate its application to a treatment site;

FIG. 7a-7e schematically illustrate the construction of another drug delivery device in accordance with the present invention and various stages when applied to a treatment site;

FIG. 8a-8c schematically illustrate a further construction of drug delivery device in accordance with the present invention particularly designed for application to a treatment site in the region of a patient's tooth and surrounding gingival and oral mucosal tissues, and various stages in the application of the device;

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
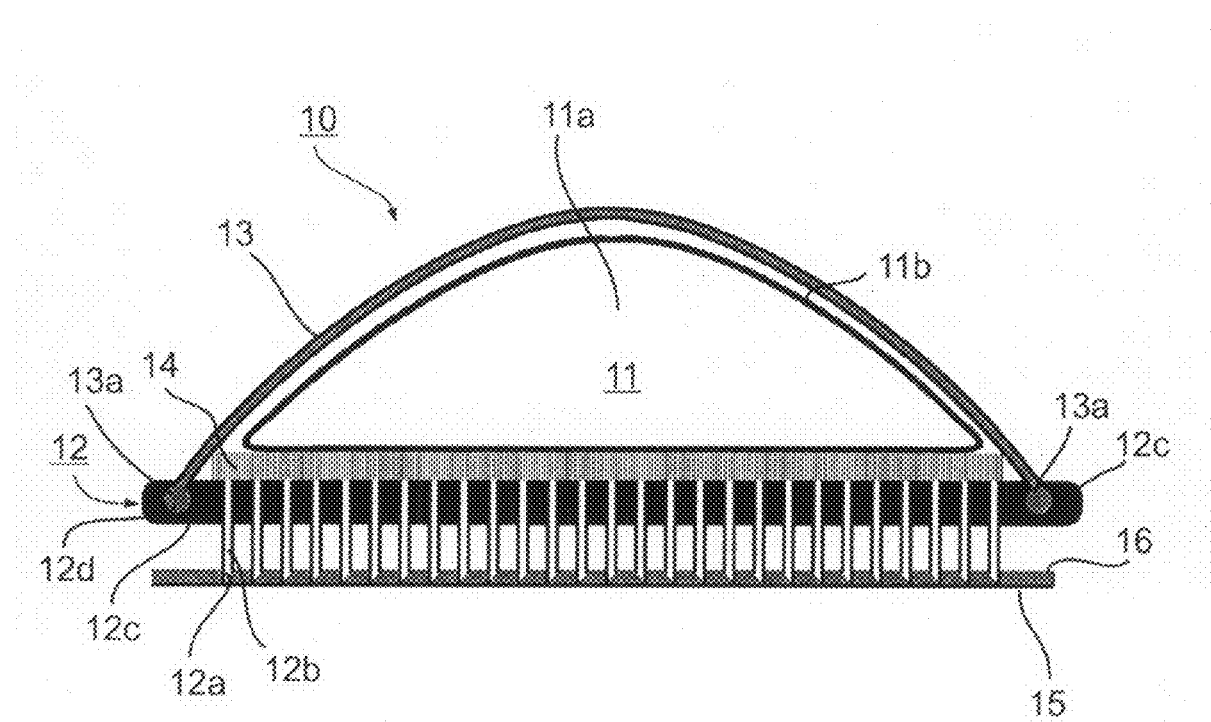
FIG. 1 is an enlarged sectional view illustrating one form of micro-needle type drug delivery device constructed in accordance with the present invention.

FIG. 1 schematically illustrates one form of drug delivery device constructed in accordance with the present invention for delivering a drug to a preselected treatment site. The illustrated device, generally designated 10, includes a capsule 11 containing a quantity of the drug 11a enclosed within a rupturable film 11b. The illustrated device further includes an array 12 of hollow micro-needles 12a formed with passageways 12b therethrough and micro-needle supporting fluid-tight matrix 12c. As will be described in greater detail below particularly with respect to FIGS. 2a-2c, it is particularly advantageous if the micro-needle array supporting matrix 12c is of a flexible nature. Array 12 is located on one side of capsule 11, and an outer deformable, fluid-tight layer 13 overlies the opposite side of the capsule. The outer deformable layer 13 has an outer peripheral edge secured to the outer peripheral edge of the micro-needle array 12 in any suitable manner to ensure a fluid-tightness, e.g. by forming the outer layer 13 with a peripheral bead 13a received within a peripheral recess 12d formed in the micro-needle array 12.

As will be described more particularly below, the illustrated device is to be located with the micro-needles 12a of array 12 facing the treatment site, such that the application of pressure to the outer layer 13 causes the micro-needles to penetrate the treatment site, and the capsule film 11b to rupture, whereby the drug is delivered via passageways 12b to the treatment site.

Although the outer deformable fluid-tight layer 13 may be composed of a wide variety of materials, it is particularly advantageous for it to be composed of an elastic material such as latex or chloroprene or butyl rubber, which is also preferably pre-tensioned. The significant advantage of having a pretensioned highly elastic cover layer is that the stored energy contained within the layer will contribute to the emptying of the rupturable capsule 11 following its initial rupture, even in the absence of any other externally applied force tending to empty the capsule. Furthermore, because outer layer 13 is attached to the perimeter of the micro-needle array substrate layer, which during application to the patient is functionally in contiguity with the underlying body surface, outer layer 13, in its natural fully collapsed state, tends to closely conform to the upper surface of the micro-needle array substrate layer, thus tending to empty the capsule to the greatest extent possible.

Figure 3:
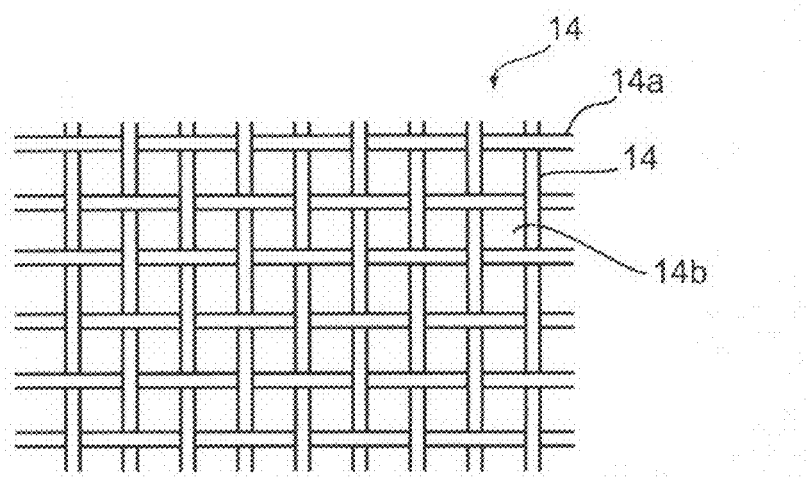
FIG. 3 is a plan view of one type of porous mesh layer in the device of FIG. 1 effective, upon rupturing the capsule, to more uniformly distribute the drug to the micro-needles and prevent clogging of the micro-needles.

The illustrated drug delivery device further includes a porous mesh layer 14 between the capsule 11 and the micro-needle array 12. Porous mesh layer 14 may be of any biocompatible natural or synthetic fibers 14a (FIG. 3), which for example, may be woven in an open mesh to define spaces 14b between the fibers, or may consist of an unstructured or non-woven mesh, e.g., of cotton or Dacron fibers. Layer 14 is effective, after the capsule film 11b has been ruptured, to uniformly distribute the drug, by a wick action, over the inner surface of the micro-needles 12a for delivery to the treatment site via the passageways 12b. Porous layer 14 is configured so as to not impede the flow of the drug. It is also effective to reduce the possibility of clogging the passageways 12b by the ruptured capsule film 11b since it tends to space the film away from the inlet ends of the passageways. That is to say, the porous mesh layer 14 is located between the capsule and the surface of the inlet ends of the micro-needles and is effective to space the inlet ends of the micro-needles from the capsule, to uniformly distribute the drug to the inlet ends of the micro-needles, and, upon rupture of the capsule film, to reduce the possibility of clogging of the passageways as the drug is delivered therethrough from the capsule to the treatment site.

Figure 4A:
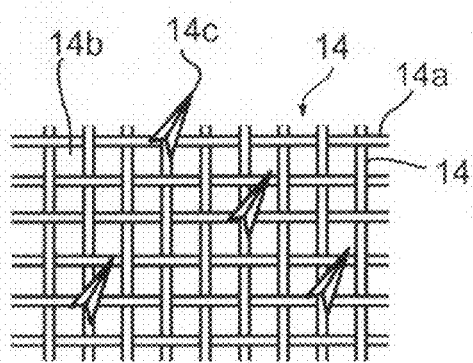
FIGS. 4a-4d illustrate variations in the construction of the device, particularly the porous mesh layer and the micro-needle array.
Figure 4B:
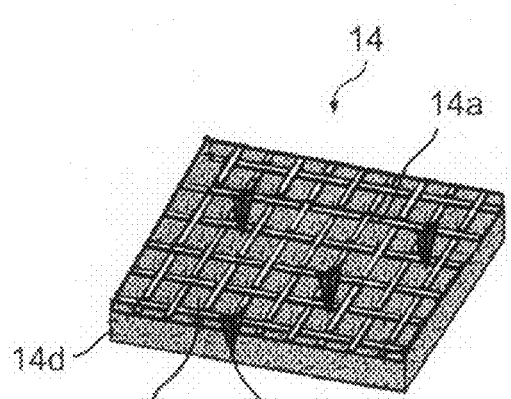
Figure 4C:
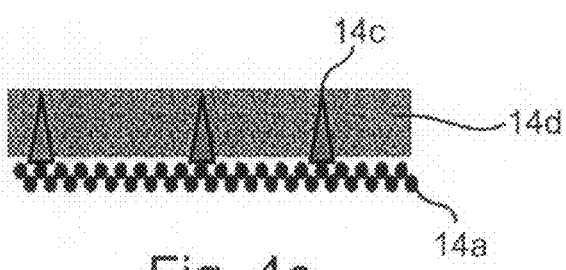

A further use to which the porous layer 14 may be put is that it may incorporate protrusions 14c on its surface facing the capsule, as shown in FIG. 4a, which may be useful in determining the site of rupture of the capsule wall 11b. A further modification would be to provide an open celled porous sponge layer 14d, which overlies the mesh layer and in its expanded state tends to prevent the protrusions 14c from directly contacting the underside of the rupturable capsule 11, is shown in FIG. 4b. FIG. 4c is a side view of the mesh 14a, protrusions 14c and sponge layer 14d, and serves to illustrate the spatial arrangement of these components.

Figure 4D:
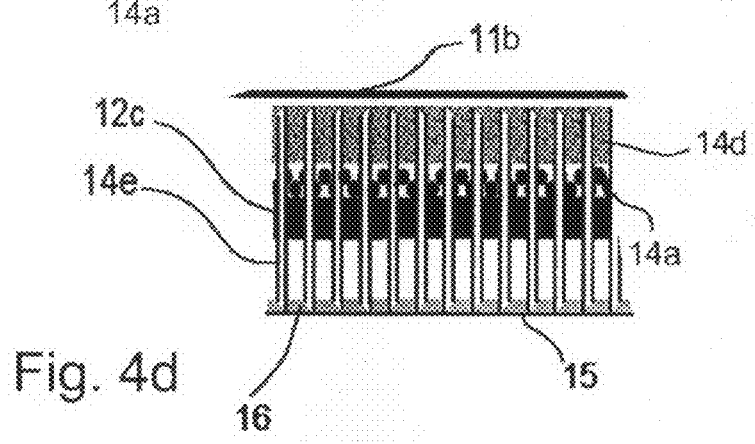

An alternative to having protrusions 14c would be to have double sided micro-needles as shown at 14e in FIG. 4d, in place of the single sided micro-needles illustrated in the accompanying figures, such that the portion of the micro-needle extending inward toward the drug containing capsule would replace elements 14c. In this case, the micro-needles would serve the dual purposes of breaching the patient's body surface and of puncturing the drug containing capsule with the added advantage of forming a direct link between the source of the drug material and the tissue site.

The drug delivery device illustrated in FIG. 1 further includes a peelable protective layer 15 covering the micro-needles 12a, and a layer of an adhesive material such as a hydrogel layer 16 over the micro-needles 12a. Hydrogel layer 16 partially fills the space between the micro-needles and the peelable protective layer 15.

Preferably, hydrogel 16 includes adhesive and also antiseptic as well as topical anesthetic properties. As will be described more particularly below with respect to FIG. 5, the construction is such that after the delivery device has been applied to deliver the drug to the treatment site, the device may be removed from the treatment site, and at least a portion of the hydrogel layer 16 will remain on and cover the treatment site. As mentioned, hydrogel layer 16 can also include an anesthetic material which may be of particular benefit in certain applications, e.g. when the device is used for treating a region of a tooth's supporting soft tissues and in particular the supporting soft tissues surrounding the tooth's roots as described below. It may also include an electrically conductive material to facilitate the drug's movement into the treatment site by iontophoresis or electroporation.

Figure 2A:
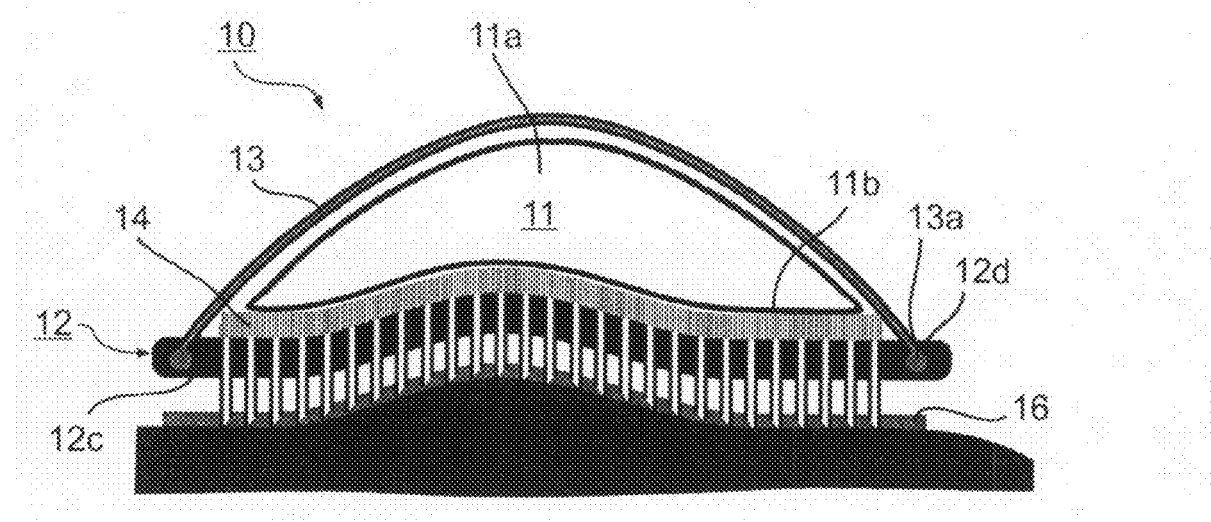
FIGS. 2a-2c illustrate variations in the construction of the drug delivery device of FIG. 1.
Figure 2B:
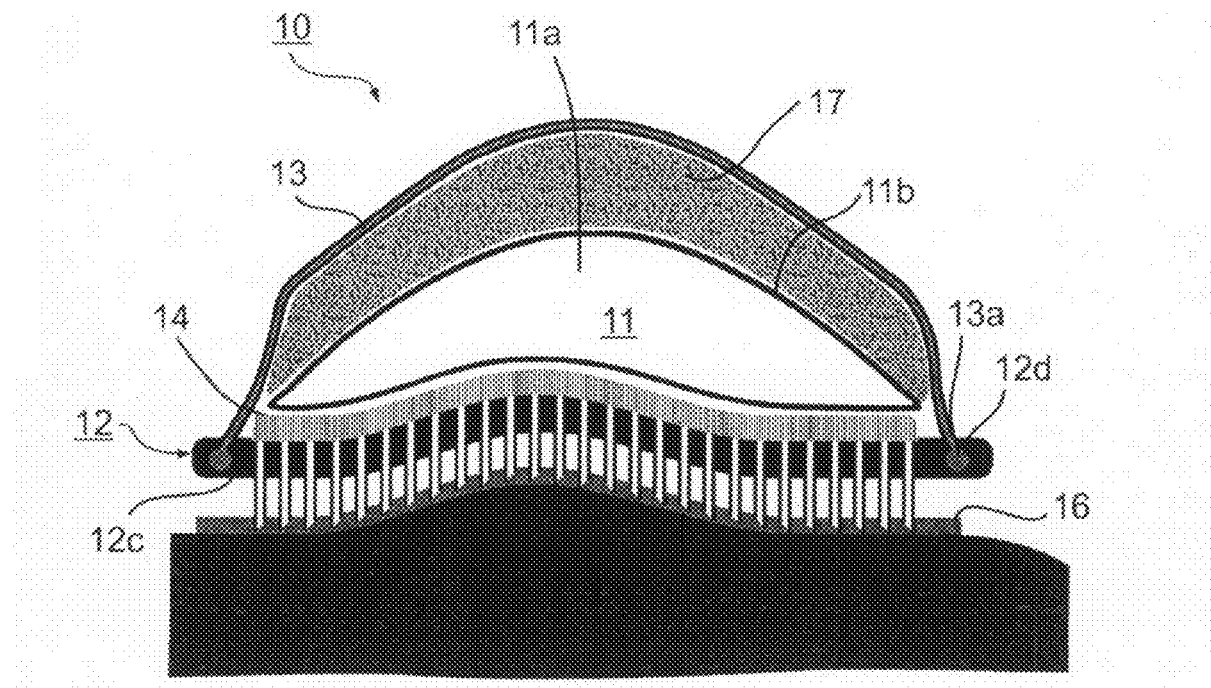

As alluded to above with respect to micro-needle array supporting matrix 12c, an important feature is derived from the combined use of a flexible substrate of the micro-needle array together with the adhesive layer which is preferably a hydrogel layer. This can provide an enhanced ability to align the micro-needles perpendicular to the underlying tissues when the tissues have a non-planar topography, as is depicted in FIGS. 2a and 2b. This is of particular importance in the case of the soft tissues surrounding the teeth, that is the oral mucosal and gingivae, which tend to be stiff and unyielding and have a complex non-planar topography.

In the case where the micro-needle supporting matrix is inherently inflexible, it may nevertheless still be possible to obtain the desired degree of flexibility of the micro-needle array by mounting small clusters of the micro-needles onto a flexible membrane while making sure that the flexible membrane surface does not occlude the micro-needle passage ways.

Figure 2C:
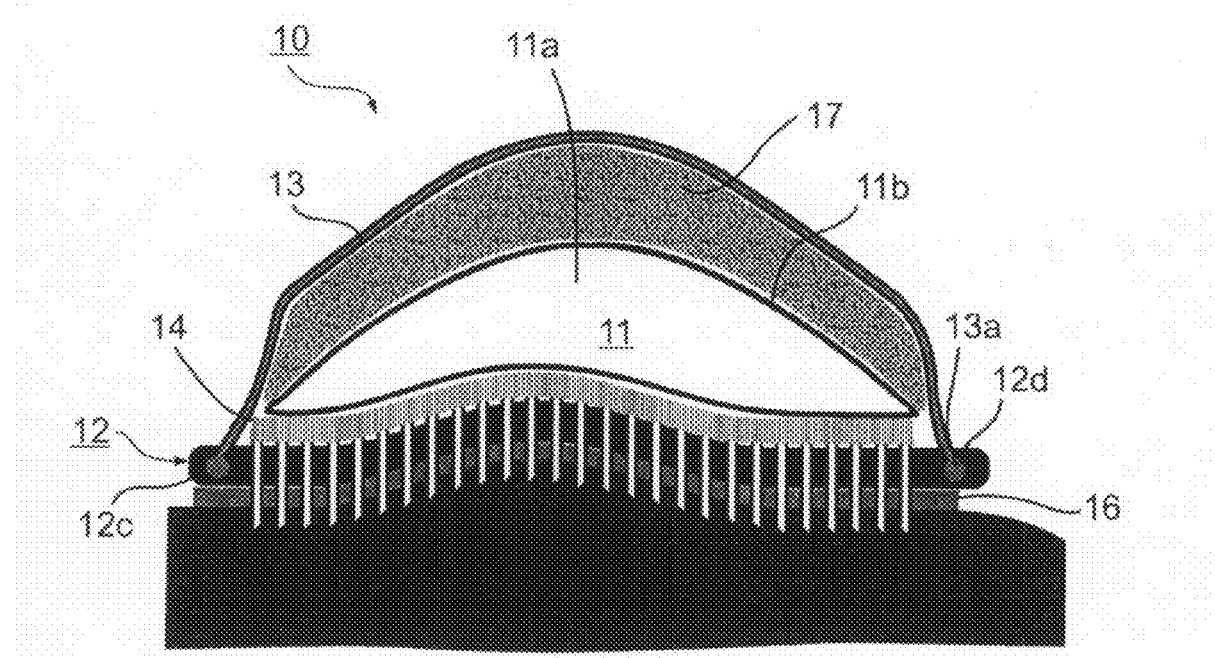

Another important benefit in the combined use of the hydrogel and flexible substrate is that the highly flexible and highly adhesive hydrogel layer readily adapts itself to the contours of the tissues and tightly adheres to them. Since the bases of the individual micro-needles are embedded in the hydrogel, the micro-needles would be also be aligned perpendicularly to the tissues if the substrate of the micro-needle array is sufficiently flexible to allow for this. When force is brought to bear on the device, the properly aligned micro-needles will thus penetrate beyond the cornified tissue layer of the body surface in an effective manner. As can be seen in FIG. 2c, when the microneedle array penetrates the outer tissue surface following the application of pressure, the hydrogel layer remains attached to the tissue surface and ultimately the free side of the hydrogel comes into adhesive contact with the matrix of the micro needle array. This ensures the effective coupling of the microneedle array supporting matrix to the tissue surface.

As described previously, after the cornified body surface layer has initially been impaled by the micro-needles 12, and after the capsule 11 has been subsequently ruptured, the continued application of force to the device will cause the fluid contents to flow through the micro-needles into the tissues.

In the case where the outer layer 13 is composed of a pretensioned elastic material, and the device is adhesively attached to the body surface using for example a hydrogel layer, it may be unnecessary for there to be a continued force brought to bear on the device to continue and ultimately complete the injection process, since the stored energy of the outer layer 13 will tend to drive the liquid contents out of the capsule while the adhesive attachment of the device to the body surface will tend to maintain an adequate coupling of the device to the body surface.

In this way, the remainder of the injection process, after the actual initiation of the process of impaling the surface and rupturing the capsule has been achieved, will proceed in a self sustained manner, that is, without the need for the operator to continue to press the device on the patient.

In situations in which the device is applied to a body region which has a complex, or otherwise non-planar topography, the effective emptying of the capsule will be aided by the addition of a closed cell, non-absorbent sponge like material, shown in FIG. 2b at 17. This is interposed between the outer cover layer 13 and the upper surface of the rupturable capsule 11, and is capable of conforming to the shape of the residual volume throughout the capsule emptying process. A compliant fluid filled bag could also used in lieu of the sponge like material to achieve the same effect.

FIG. 5 schematically illustrates various stages in the application of the drug delivery device 10 to a treatment site TS. Thus, after the protective layer is removed from pressure-sensitive adhesive 16a on the outer surface of the device opposite to the micro-needle side as shown at FIG. 5(a), the device is adhesively attached to the operator's finger as shown at FIG. 5(b). Subsequently, protective layer 15 is removed from hydrogel layer 16 covering the micro-needle array 12, and device 10 is placed on the treatment site TS with micro-needles 12a in contact with the treatment site, as shown at FIG. 5(c); finger pressure is then applied, as shown at FIG. 5(c), to cause the micro-needles 12a to penetrate the treatment site and the capsule film 11b to rupture, thereby forcing the drug 11a within the capsule through the passageways 12b of the micro-needle array, as shown at FIG. 5(c); and then the device is removed from the treatment site, to thereby leave the hydrogel layer 16 covering the treatment site, as shown at FIG. 5(d). The last step, shown at FIG. 5(d), may be effected by merely finger-grasping the device and removing it from the treatment site; or as illustrated in this case, the pressure-sensitive adhesive on the outer surface of the device permits removal of the device from the treatment site by adhesion with the user's finger.

Initial attachment of the device to the operators finger using the pressure-sensitive adhesive prior to its application to the treatment site, may facilitate accurate placement of the device and promote stable operator pressure application during the injection process.

As described above, the provision of the porous layer 14 between the capsule 11 and the micro-needle array 12 better assures that upon rupture of the capsule film 11b, the drug 11a within the capsule will be uniformly distributed over the inner surface of the micro-needle array 12 for transfer via passageway 12b to the treatment site. The provision of mesh layer 14 also reduces the possibility of clogging of the passageways 12b by the capsule film 11b when the film is ruptured.

As also described above, the provision of the hydrogel layer 16, which is preferably retained over the treatment site as shown at FIG. 5(d), not only provides antiseptic protection and possibly anesthetic conditioning to the treatment site, but also covers the treatment site to block any outflow of the drug delivered to the treatment site.

FIG. 6 illustrates a variation in the construction of the drug delivery device 10, in that the outer flexible layer 13 of the device is fixed to, or is integrally formed with, a finger sleeve 20 receivable over the user's finger to facilitate the application of the device to the treatment site, and its removal from the treatment site. The device illustrated in FIG. 6 is otherwise of the same construction and may be used in the same manner as described above with respect to FIGS. 1-5.

FIG. 7 illustrates another construction of drug delivery device in accordance with the present invention and the manner of using it for delivering the drug to a treatment site. The device illustrated in FIG. 7, as shown at (a), also includes a drug capsule 31, a micro-needle array 32, an outer deformable layer 33, and an open mesh layer 34 between the capsule and the micro-needle array 32. In this particular case, the capsule 31 has a height substantially larger than its length and width, however the relative dimensions may be varied. In addition, the outer deformable layer 33, instead of being of a pliable plastic material as described above, is of a bellows construction to permit it to be deformed in order to rupture the capsule for delivering the drug therein to the treatment site via the micro-needles of the micro-needle array 32. To facilitate the deformation of the outer layer 33, it preferably carries, or is integrally formed with, a rigid or semi-rigid (stiff) center disc 36 for convenient engagement by the user's finger to apply the pressure which causes the micro-needles to penetrate the treatment site, and also the drug capsule to rupture and thereafter causes the liquid contents of the capsule to continue to be impelled into the tissue The space between capsule 31 and the outer bellows layer 33 may be filled with sponge rubber or other compressible filler material 37.

As shown in FIG. 7b, drug delivery device 30 may further include an adhesive tape 38, with or without a semi rigid covering surface, applied over the center disc 36 of the device. Adhesive tape 38 with or without a semi rigid covering surface includes lateral extension 38a on its opposite sides coated with a pressure-sensitive adhesive 38b so as to retain the device over the treatment site TS after applied thereto, as shown in FIG. 7c. A body of compressible sponge, or an expansion spring may also be placed between the center disk 36 and the underside of adhesive tape 38, with or without a semi rigid covering surface. The benefit of this addition is that following the micro-needle's penetration of the treatment site and the drug containing capsule's rupture during the initial application process, and following subsequent adhesion to the body surface, the compressed sponge or expansion spring would further contribute to the continuing provision of a predetermined, and substantially constant driving force for causing the liquid contents of the capsule to continue to be impelled into the tissue.

The above described arrangement may also be used in conjunction with the types of drug delivery devices described above. FIG. 7d shows the manner in which this may be applied. A semi rigid covering surface which includes lateral extension 38a on its opposite sides coated with a pressure-sensitive adhesive 38b, overlying a rigid or semi-rigid (stiff) central disc 36 which is in turn attached to a compressible sponge or expansion spring 39, optionally with a further disk 36 at its opposite end. This is in turn applied to any of the units of the type described in FIGS. 1 and 2 for the purpose of providing an ongoing driving force for causing the liquid contents of the capsule to continue to be impelled into the tissue after the micro-needles have initially penetrated the treatment site, and the drug capsule has been ruptured and adhesive surface 38b is attached to the tissue surface, as mentioned above. Following adhesion to the body surface, the compressed sponge or expansion spring 39 provides a continuous predetermined and substantially constant driving force for causing the liquid contents of the capsule to continue to be impelled into the tissue.

FIG. 8 illustrates another construction of a drug delivery device for delivering a drug, such as an anesthetic or antibiotic, to the gingival tissue and/or oral mucosal tissues of a patient's mouth during a dental treatment, and also several phases in such a dental treatment. The construction illustrated in FIG. 8, and therein generally designated 40, includes a housing 41, open at the upper end, and lined on its inner surface with by an elastic sponge like material 45. Housing 41 is of a generally splayed configuration and is configured to be applied to opposing sides of the tooth (or other body part) with the array of micro-needles facing tissue at the treatment site to which the drug is to be delivered. A drug delivery device 10a, 10b, corresponding to device 10 in FIG. 1, is carried on the inner surfaces of the opposing walls of the housing with the micro-needle array 12 of each device facing inwardly so as to be engageable with gingival/oral mucosal tissue on the opposite sides of the tooth being treated. For example, the outer deformable layer 13 of each drug delivery device 10 may be secured in any suitable manner to, or integrally formed with, the sponge layer 45 lining the inner surface of housing 41, preferably in a manner allowing each device 10 to pivot in order to accommodate itself to the gingival surface to be engaged by its micro-needle array 12.

The assembly 40 illustrated in FIG. 8 further includes an outer sleeve 42 telescopically receiving housing 41. Outer sleeve 42 is configured with respect to the housing such that axially displacing the outer sleeve towards the housing open end, by for example manual manipulation, or biting action due to the closing of the jaws, causes opposing sides of the splayed housing 41 to converge and the array of micro-needles 12 in each device 10a, 10b to penetrate the gingival tissue at the treatment site. It also causes the capsule 11 within the respective delivery device to rupture and thereby to deliver the drug to the gingival and/or oral mucosal tissue, as shown at (a), (b) and (c) in FIG. 8.

Figure 9:
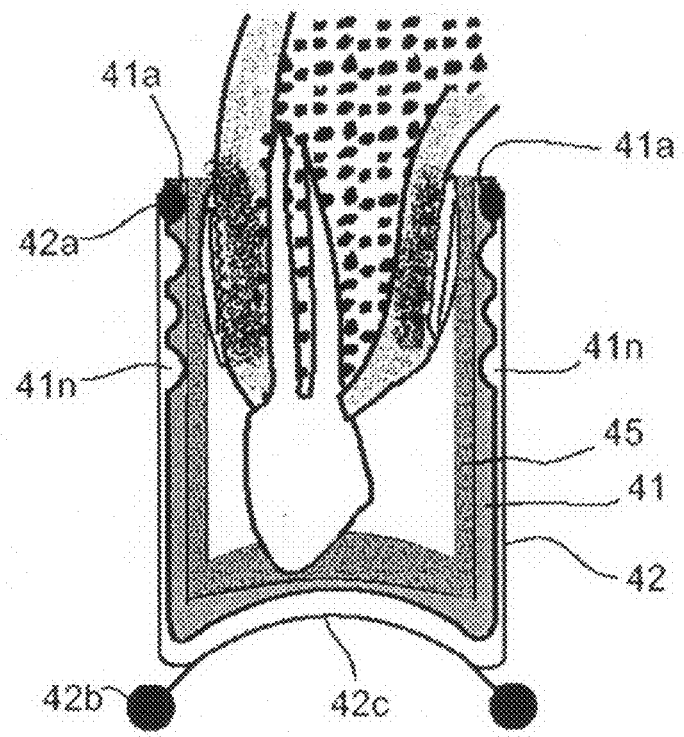
FIG. 9 schematically illustrates a modification in the construction of the drug delivery device of FIG. 6.

FIG. 9 illustrates a drug delivery assembly similar to that of FIG. 8, but including a releasable retainer device for retaining the outer sleeve 42 in its axially-displaced position with respect to housing 41, and for selectively releasing the outer sleeve from its retained position. Thus, as shown in FIG. 9, housing 41 is formed with a plurality of annular recesses 41a-41n spaced along its length for selectively receiving a rib 42a formed on the inner surface of the sleeve 42 adjacent its upper open end. Sleeve 42 is somewhat elastic to permit its rib 42a to snap into a selected recess 41a-41n of housing 41, and also to be forcefully unseated from the recess. The lower end of sleeve 42 may be formed with another annular rib 42b squeezable between two fingers of the user in order to deform the bottom wall 42c, and thereby to facilitate the unseating of rib 42a from a selected recess 41a-41n.

Figures 10A, 10B, 10C:
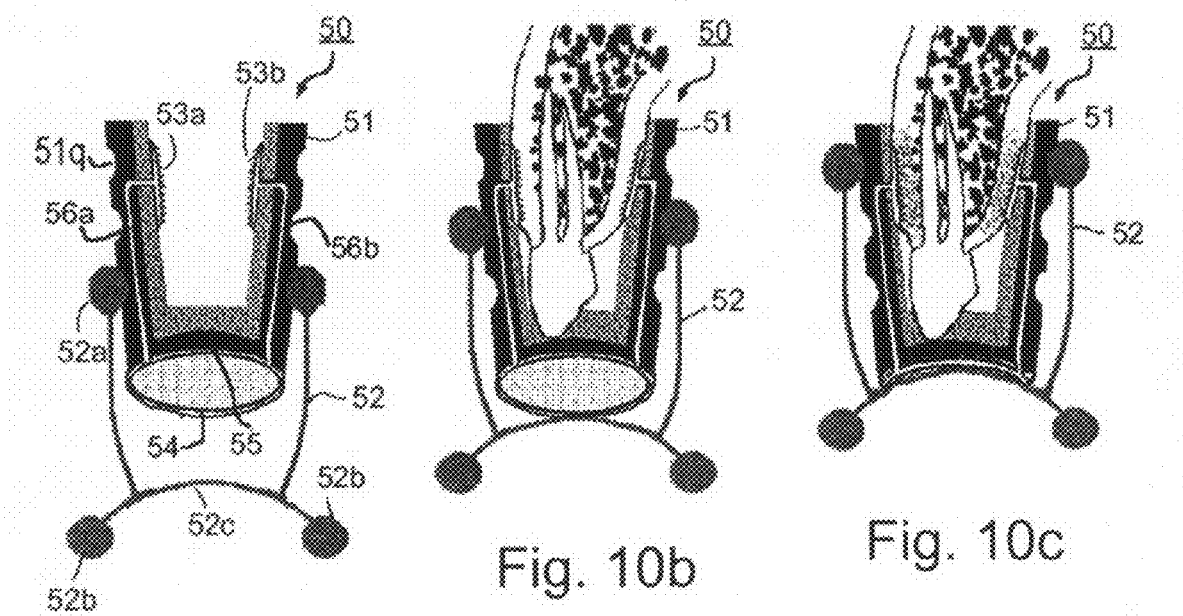
FIGS. 10a-10c schematically illustrate a modification in the construction of the device of FIG. 9 and various stages in its use.

FIG. 10 illustrates a drug delivery device, generally designated 50, similar to that of FIG. 9, and various stages in its use as illustrated in FIG. 8. The device illustrated in FIG. 10 also includes a splayed housing 51 open at one end and configured to be applied to a patient's tooth and supporting soft tissues, and an outer sleeve 52 telescopically receiving the housing and axially displaceable with respect to the housing for activating the device. The illustrated device further includes a micro-needle array 53a, 53b carried on each of the opposite faces of the inner surface of housing 51, and a capsule 54 containing a quantity of the drug to be delivered enclosed within a rupturable film.

In the drug delivery device illustrated in FIG. 10, however, the capsule 54 is received within a cavity 55 formed in the end wall closing the bottom of housing 51. Cavity 55 communicates with each of the two micro-needle arrays 53a, 53b via passageways 56a, 56b formed in the side walls of housing 51.

Housing 51, and sleeve 52 telescopically received thereover, are otherwise similarly constructed as described above with respect to FIGS. 8 and 9. Thus, housing 51 includes a plurality of annular recesses, e.g., 51q; and sleeve 52 includes an annular rib 52a receivable within a selected recess for releasably retaining the sleeve in an actuated position on the housing. Sleeve 52 is also formed with the annular rib 52b squeezable by the user's fingers in order the release the sleeve from the housing. In this case, however, the bottom wall 52c of sleeve 52 is configured such that, after the sleeve has been moved from a lower position, as shown at (a), to an intermediate position to cause the micro-needle arrays 53a, 53b to pierce the tissue at the treatment site, as shown at (b) in FIG. 10, the sleeve may be further moved to its uppermost position, wherein its rib 52a seats in the upper annular recess 51a, to cause the bottom wall 52c of the sleeve to engage the capsule 54 and to rupture the capsule, as well as to force its contents through channels 56a, 56b to the micro-needle arrays 53a, 53b as shown at (c) in FIG. 10.

The FIG. 10 construction thus not only better assures that the capsule will be ruptured only after the micro-needle arrays penetrate the tissue at the treatment site, but also enables the housing to be of a more compact construction since it accommodates the capsule in the end wall of the housing, rather than at the two side walls adjacent to the micro-needle arrays.

Figure 11A:
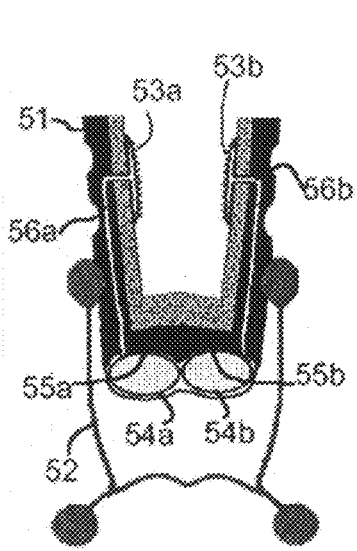
FIG. 11a-11c schematically illustrate a modification in the construction of the device of FIG. 10 and various stages in its use.
Figure 11B:
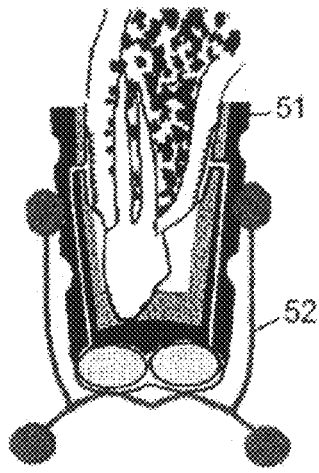
Figure 11C:
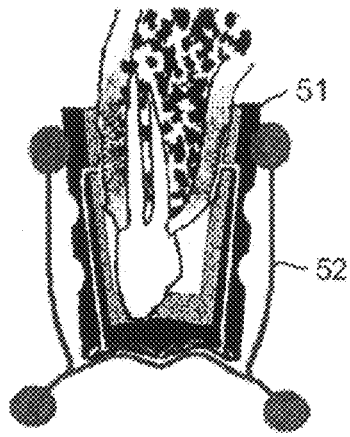

FIG. 11 illustrates a drug delivery device of similar construction as in FIG. 10, and various stages in its use as described above with respect to FIG. 10, except that instead of providing the housing 51 with a single cavity 55 for receiving a single capsule 54, the housing is provided with two cavities 55a, 55b, each for receiving a separate capsule 54a, 54b, each communicating with one of the passageways 56a, 56b with one of the micro-needle arrays 53a, 53b. Providing a separate capsule for each micro-needle array better assures a more even distribution of the drug to the treatment site via the two arrays.

Figure 12:
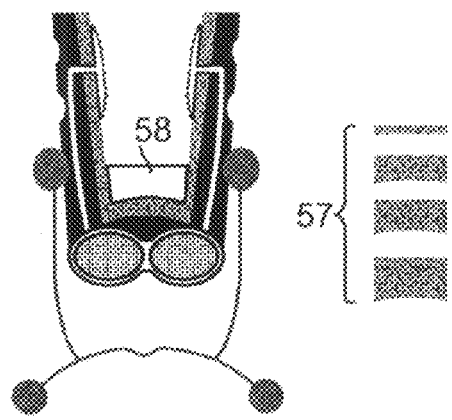
FIG. 12 illustrates a modification in the construction of the device of FIG. 11.

A feature of all the designs illustrated in FIGS. 8-11 is the ability to vary the position of the micro needle arrays with respect to the bottom (crown) of the teeth. It is important to be able to accurately position the micro-needles over the supporting tissues surrounding the teeth, i.e. the gingivea and oral mucosal tissues; however this location relative to the tooth's crown the can vary from case to case. In order to be able to adjust the height of the micro-needles relative to the tooth crown, a series of sponge pad inserts 57 of different thicknesses may be selectively inserted into the space 58, as shown in FIG. 12.

By using hydrogel bodies with increased thickness, which are saturated with a solution of an appropriate medication (such as the anesthetic lidocaine), and a source of DC current wired to the hydrogel bodies, it is possible to iontophoretically drive significant amounts of the medicine into the underlying tissues, even in the absence of the micro-needle and drug containing capsule arrangements, when using supporting devices of the type illustrated in FIGS. 8-12, wherein the micro-needle arrays are replaced by the hydrogel bodies with increased thickness, which are saturated with a solution of an appropriate medication. In this manner, the application of electrical current would be initiated only after a predefined level of pressure had been reached during the clamping process described for the designs of FIGS. 8-12.

If the two sides of the devices are to be used for this purpose, then the polarity of the DC current may be reversed at appropriate intervals to cause the medicine to be delivered to both sides. Alternatively, a third electrode to be applied at a different body site, may be used, in which case the iontophoretic delivery may be applied simultaneously to both sides of the tooth or teeth being treated.

Iontophoresis could be used in the manner described above, or could be used in conjunction with the hollow micro-needle array and capsule arrangement as a source of the drug.

It is also possible to simply use hydrogel bodies, which are saturated with a solution of an appropriate medication, in combination with either solid or hollow micro-needle, when using any of described devices in order to augment the delivery of the drug. In this manner, the perforation of the body surface by the micro-needles and the positive force applied to the hydrogel body or bodies would augment the transfer of the drug from the hydrogel source to the underlying tissues by making the body surface more permeable, and by applying a positive pressure gradient to the drug held in the hydrogel. This process could be performed either with or without drug containing capsule arrangements shown in those figures. This most particularly applicable in the cases of those designs having a compressible sponge component, i.e. those shown in FIGS. 2 and 5-12 inclusive, which provide ongoing force even in the absence of user applied force, following their initial application.

Drug coated solid micro-needles known to the art could likewise be used for trans-gingival drug delivery when using supporting devices of the type illustrated in FIGS. 8-12. Likewise, they could be used for surface drug delivery when using supporting devices of the type illustrated in FIG. 1, FIGS. 2a-2c and in FIGS. 5-7, and would be especially effective when used in combination with drug saturated hydrogels as described above.

Figure 13:
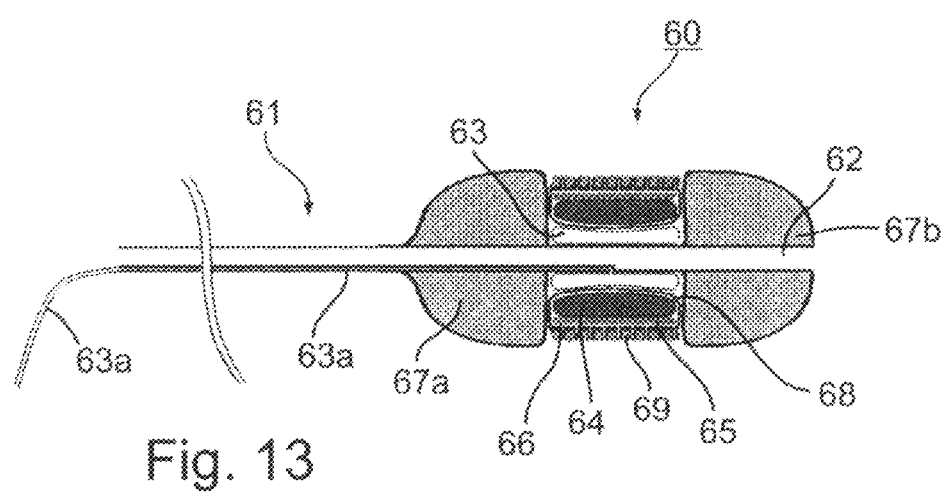
FIG. 13 schematically illustrates another drug delivery device constructed in accordance with the present invention for delivering a drug to a preselected treatment site within a lumen of a patient's body.

FIG. 13 illustrates a drug delivery device constructed in accordance with the present invention particularly useful for delivering a drug beyond the surface of an internal body lumen, such as a wall of the respiratory tract, of the alimentary tract, of the urogenital tract, or of an arterial or a venous blood vessel. In this case, the drug delivery device is carried by a catheter to enable its manipulation to the treatment site, and is activated at the treatment site by the inflation of a balloon.

As shown in FIG. 13, the drug delivery device, therein generally designated 60, includes a carrier member in the form of a catheter tube 61 formed with a central passageway 62. Passageway 62 may serve for the insertion of a guide wire, as a conduit for the tube or tubes 63a inflating the balloon or balloons, for the administration of materials such as contrast media or for the administration of drugs to the distal intraluminal space, as well as for the insertion of an endoscope, etc.

The drug delivery device 60 is sized for insertion into the respective lumen. It includes an inner balloon 63 which is connected to tube 63a for facilitating filling or emptying of the balloon and is attached to at least one drug delivery device of the type described above. The illustrated drug delivery device comprises a rupturable film capsule or closed bag 64 containing the drug to be administered, a mesh layer 65 thereover, an outer array of micro-needles 66 oriented such that the micro-needles face the treatment site and an outer deformable layer 68 overlying the opposite side of the capsule. The outer deformable layer 68 has an outer peripheral edge secured to the outer peripheral edge of the micro-needle array 66. As stated, the micro-needle array, drug filled capsule, mesh layer and outer cover construction described above overlying balloon 63 are essentially similar to the various devices illustrated in FIGS. 1 and 2 above.

Drug delivery device 60 further includes a pair of contoured abutments 67a, 67b, straddling the opposite sides of the foregoing elements to facilitate the manipulation of the drug delivery device through the lumen to the treatment site.

To further facilitate the unimpeded transfer of the drug delivery device to the intended treatment site, and to avoid unintentional contact between the micro needles and the lumen surface during the process of transferring the device to the intended treatment site, a compressible sponge layer 69 is placed between said micro-needles such that its upper side extends to the top of the micro-needles. Compressible sponge layer 69 is firmly adhered to the micro-needle array to prevent its dislodgement in the lumen.

It will be appreciated that balloon 63 is in a deflated condition during the manipulation of the drug delivery device 60 to the treatment site. Upon reaching the treatment site, balloon 63 is inflated to thereby cause the micro-needles to compress sponge layer 69 and to penetrate the tissue at the treatment site, and the capsule 64 to rupture and to deliver the drug to the treatment site via the passageways of the micro-needle array, as described above. Following completion of the drug delivery process, micro-needle array 66 is withdrawn from the lumen wall by actively deflating balloon 63 so as to cause the micro-needle array to retract, and allow sponge layer 69 to then re-expand to again prevent unintentional contact between the micro needles and the lumen surface during the process of withdrawing the device.

The foregoing elements 63-69 of the drug delivery device are preferably of an annular configuration so as to uniformly distribute the drug to an annular surface at the treatment site. It will be appreciated, however, that the foregoing elements may be of a non-annular or segmented configuration, e.g., where the drug is to be delivered to a non-annular region. It will be further appreciated that more than a single micro-needle based drug delivery unit may be employed, that these may be of varying sizes, and that this invention could be implemented using MEM (microelectronic machining) technology.

Accordingly, the invention has been described with respect to several preferred embodiments, it will be understood that these are set forth merely for purposes of example, and that many other variations, modifications and applications of the invention may be made.

What is claimed is:

1. A drug delivery device for delivering a drug to a preselected treatment site, comprising:
    a capsule having a rupturable film enclosing a quantity of the drug to be delivered;
    an array of micro-needles mounted on a supporting matrix carried by said device,
    said micro-needles being formed with inlet ends facing the capsule, outlet ends to face the treatment site when the device is located with the micro-needles facing the treatment site, and passageways connecting said inlet and outlet ends, whereby the application of pressure to the device causes the outlet ends of the micro-needles to penetrate the treatment site, the capsule to rupture, and the inlet ends of the micro-needles to deliver the drug via said passageways to the treatment site; and
    a porous mesh layer between the capsule and the complete surface of the inlet ends of the micro-needles effective to space the inlet ends of the micro-needles from said capsule, to uniformly distribute the drug to the inlet ends of the micro-needles by a wick action, and, upon the rupture of the capsule film, to reduce the possibility of clogging of the passageways as the drug is delivered therethrough from the capsule to the treatment site;
    wherein the device further comprises an outer deformable fluid-tight layer overlaying said capsule and having an outer peripheral edge hermetically secured to the outer peripheral edge of the array of micro-needles so as to enclose said capsule between said array of micro-needles and deformable fluid-tight layer, said deformable fluid-tight outer layer being deformable by pressure to permit rupturing said capsule by the application of pressure thereto; and
    wherein said outer deformable fluid-tight layer is of an elastic material which is pre-tensioned such as to enhance the flow of the drug into said passageways upon rupture of said capsule film.

2. The apparatus according to claim 1, wherein said porous mesh layer includes natural or synthetic fibers woven in an open mesh.

3. The device according to claim 1, wherein the device further comprises a peelable protective layer covering said micro-needles.

4. The device according to claim 3, wherein said device further comprises a layer of an adhesive over and between said micro-needles and covered by said peelable protective layer.

5. The device according to claim 3, wherein said device further comprises a layer of a hydrogel over and between said micro-needles and covered by said peelable protective layer.

6. The device according to claim 5, wherein said layer of hydrogel includes adhesive and antiseptic properties such that, upon removal of the device from the treatment site, after removal of the protective layer and application of the device to the treatment site, at least a portion of the hydrogel layer remains on and covers the treatment site.

7. The device according to claim 5 wherein said layer of hydrogel further includes anesthetic properties.

8. The device according to claim 1, wherein the device further comprises, between said outer deformable layer and said capsule, a closed cell, non-absorbent sponge body which is compressible to facilitate deformation of the outer deformable layer and rupture of said capsule and to enhance the flow of the drug into said passageways upon rupture of said capsule film.

9. The device according to claim 1, wherein the device further comprises, between said outer deformable layer and said capsule, a compliant, fluid-filled bag which is compressible to facilitate deformation of the outer deformable layer and rupture of said capsule and to enhance the flow of the drug into said passageways upon rupture of said capsule film.

10. The device according to claim 1, wherein the device further comprises a rigid or semi-rigid finger piece carried centrally of said outer deformable layer.

11. The device according to claim 10, wherein said rigid or semi-rigid finger piece carried centrally of said outer deformable layer has lateral extensions coated with an adhesive for fixing the device to the treatment site.

12. The device according to claim 1, wherein said device further includes a compressible element between said finger piece and said outer deformable layer, which compressible element, when compressed, produces a continuous force pressing said micro-needles into said treatment site and effective emptying of the said capsule.

13. The device according to claim 1, wherein the device further comprises an adhesive tape secured to said outer deformable layer and having lateral extensions coated with an adhesive for fixing the device to the treatment site.

14. The device according to claim 1, wherein said supporting matrix array of micro-needles is flexible to permit the device to conform to the surface of the treatment site.

15. The device according to claim 14, wherein said device further comprises a peelable protective layer, and a layer of an adhesive over and between said micro-needles and said peelable protective layer.

16. The device according to claim 1, wherein said micro-needles are pointed at their opposite ends, said device further comprising a sponge layer between said micro-needles and said capsule.

17. The device according to claim 1, wherein the device further comprises a finger sleeve receivable over a finger of a user to facilitate the application of the device to the treatment site.

18. The device according to claim 1, wherein the device is sized and configured for delivering the drug to a preselected treatment site within a body lumen wall, said device further comprising a balloon which is inflatable at the treatment site to produce the pressure to cause said array of micro-needles to penetrate the treatment site and the capsule to rupture.

19. The device according to claim 18, wherein said device further comprises a catheter tube serving as a carrier member sized and configured to receive within it said capsule and said array of micro-needles, to be inserted into the lumen, to be manipulated to the treatment site; and to inflate and deflate said balloon.

20. The device according to claim 19, wherein the device further comprises, between said outer deformable layer and said capsule, a compliant, fluid-filled bag which is compressible to facilitate deformation of the outer deformable layer and rupture of said capsule and to enhance the flow of the drug into said passageways upon rupture of said capsule film.

21. The device according to claim 19, wherein the device further comprises a passageway through said catheter tube for receiving a guide wire to facilitate manipulating the catheter tube to the treatment site.

22. The device according to claim 21, wherein said passageway is sized to facilitate the instillation therethrough of fluids to be delivered to the distal intra-luminal space and also to receive an endoscope.

23. The device according to claim 19, wherein said device further comprises a compressible sponge layer between said micro-needles such that the upper side of the sponge layer extends to the top of the micro-needles to prevent unintentional contact between the micro needles and the lumen surface during the process of manipulating the device to the intended treatment site, said compressible sponge layer being firmly adhered to the micro-needle array to prevent its dislodgement in the lumen.

24. The device according to claim 1 further comprising a housing carrying said capsule and said array of micro-needles; and said outer deformable fluid-tight layer; said housing being open at one end and being of a generally splayed configuration and configured to be applied to opposing sides of a tooth with said array of micro-needles facing tissue at the treatment site to which the drug is to be delivered.

25. The device according to claim 24, wherein said device further comprises an outer sleeve telescopically receiving said housing and configured with respect to said housing such that axially displacing the outer sleeve towards the housing open end causes opposing sides of said splayed housing to converge and the array of micro-needles to penetrate tissue at the treatment site, and the capsule to rupture to deliver the drug to said tissue.

26. The device according to claim 25, wherein said housing includes an end wall having an outer surface formed with a cavity for receiving said capsule, and a side wall mounting said array of micro-needles on an inner surface thereof and formed with a passageway for conducting liquid drug from said capsule after rupture thereof to said array of micro-needles.

27. The device according to claim 25, wherein said housing includes a releasable retainer device for retaining the outer sleeve in its axially-displaced position, and for selectively releasing the outer sleeve from its axially-displaced position.

28. The device according to claim 25, wherein said device further includes a pad insert selectively insertable within said housing for engagement with the crown of the patient's tooth.

29. The device according to claim 25, wherein said housing includes two arrays of micro-needles, one mounted on the inner surface of each of two opposite sides, such that the axial movement of said outer sleeve towards said housing causes the two arrays of micro-needles to penetrate the opposite surfaces of the gingival tissue.

30. The device according to claim 29, wherein said housing is lined on its inner surface by a sponge layer, and wherein said capsule and said array of micro-needles and said outer deformable fluid-tight layer are secured thereto, effective upon convergence of said splayed housing due to said axial displacing of the outer sleeve towards the housing open end, to allow said micro-needle array to pivot in order to accommodate itself to the tissue surface.

* * * * *